United States Patent [19]

Kitagawa et al.

[11] Patent Number: 4,462,896

[45] Date of Patent: Jul. 31, 1984

[54] METHOD OF REMOVING ARSENIC IN HYDROCARBONS

[75] Inventors: Hiroshi Kitagawa; Teruyuki Onodera, both of Takaishi; Toshiyuki Fukushima, Izumi; Yoriyuki Hayashi, Shimonoseki, all of Japan

[73] Assignees: Osaka Petrochemical Industries Ltd.; Toyo CCI Kabushiki Kaisha, both of Tokyo, Japan

[21] Appl. No.: 436,707

[22] Filed: Oct. 26, 1982

[51] Int. Cl.³ .................. C10G 29/02; C10G 29/04
[52] U.S. Cl. .................. 208/253; 208/251 R; 585/823
[58] Field of Search .............. 208/253, 251 R; 423/617, 210 M; 585/823

[56] References Cited

U.S. PATENT DOCUMENTS

| | | | |
|---|---|---|---|
| 798,216 | 8/1905 | Scharff | 423/210 M |
| 2,778,779 | 1/1957 | Donaldson | 585/751 |
| 3,069,350 | 12/1962 | Romella | 208/253 |
| 3,933,624 | 1/1976 | Myers | 208/253 |
| 3,954,603 | 5/1976 | Curtin | 208/253 |
| 4,003,829 | 1/1977 | Burger et al. | 208/253 |
| 4,045,331 | 8/1977 | Ward | 208/253 |
| 4,051,022 | 9/1977 | Myers et al. | 208/253 |

FOREIGN PATENT DOCUMENTS

| | | | |
|---|---|---|---|
| 2726490 | 6/1977 | Fed. Rep. of Germany | 208/251 R |
| 814856 | 3/1979 | U.S.S.R. | 423/617 |

Primary Examiner—Delbert E. Gantz
Assistant Examiner—Cynthia A. Prezlock
Attorney, Agent, or Firm—Ladas & Parry

[57] ABSTRACT

Method of removing arsenic in hydrocarbons such as LPG, wherein arsenic compounds in the gaseous hydrocarbon are reacted with a metal oxide catalyst and adsorbed on the catalyst and partially oxidized by the catalyst.

5 Claims, 3 Drawing Figures

METHOD OF REMOVING ARSENIC IN HYDROCARBONS

BACKGROUND OF THE INVENTION

The present invention relates to a method of removing arsenic, particularly arsines, in hydrocarbons particularly gaseous hydrocarbons such as LPG.

Recently, accompanying the effective utilization and quality improvement of heavy fractions of crude oil, reforming conversion of the heavy fractions to gasoline by means of fluidized bed catalytic cracking apparatus has been put into practice. $C_3$ and $C_4$ LPG fractions, particularly $C_3$ LPG fraction, produced as by products of the conversion process, sometimes contain hydrogen arsenide; depending on the kind of crude oil.

When using $C_3$ LPG fraction in industrial uses, it is usually separated into a propylene fraction and a propane fraction by a distillation process, whereby the hydrogen arsenide is distributed in the propylene fraction. The hydrogen arsenide in the propylene fraction functions as a catalyst poison in a later reaction process, so that removal thereof is a pressing problem.

Heretofore, there have been proposed many methods of removing arsenic contained in petroleum fractions. Typical examples thereof are: U.S. Pat. No. 3,093,574 wherein liquid naphtha containing arsenic is treated by silica gel impregnated with sulfuric acid; U.S. Pat. No. 2,779,715 wherein arsenic in a petroleum fraction is treated by an alkaline metal or alkaline earth metal salt in the presence of a catalyst consisting of noble metal and alumina; U.S. Pat. No. 2,781,297 wherein arsenic in a petroleum fraction is treated by a salt of copper or a metal which has a smaller electromotive force than copper; and Japanese patent application No. 55/55,511/77 (laid-open No. 143,607/78) wherein arsenic in a petroleum fraction is subjected to oxidization treatment by means of an organic oxidizing material or oxygen-containing gas and the resultant oxidized arsenic is separated and removed by distillation. However, these methods have various drawbacks in that a minor content of arsenic is difficult to remove, investment cost accompanying pre-treatment and post-treatment is considerable, and production preparation costs of arsenic-removing agent are rather expensive, and a polymer is liable to be produced because of polymerization when treating a petroleum fraction containing highly reactive olefin and diolefin.

SUMMARY OF THE INVENTION

The present invention obviates the above-mentioned drawbacks of conventional methods.

An object of the present invention is to provide a method of removing arsenic in hydrocarbons such as LPG, wherein arsenic compounds in the gaseous hydrocarbon are reacted with a metal oxide catalyst and adsorbed on the catalyst and partially oxidized by the catalyst.

Another object of the present invention is to provide a method of removing arsenic in hydrocarbons such as LPG, wherein an arsenic compound in a gaseous hydrocarbon is reacted with a metal oxide catalyst, adsorbed on the catalyst and partially oxidized by the catalyst, the catalyst consisting mainly of at least one metal oxide selected from the group consisting of manganese oxide, copper oxide and a mixture thereof.

Other objects and advantages of the present invention will be apparent from the following description and claims.

DETAILED EXPLANATION OF THE INVENTION

The inventors have made many experiments and studies on catalysts which are effective for removing arsenic compounds, particularly arsines such as $AsH_3$, $CH_3AsH_2$ and the like, in hydrocarbons from the view point that the removal of arsenic compounds is necessary, leading to a finding that metal oxides, particularly manganese oxide, copper oxide and mixtures thereof, are extremely useful as catalysts.

Namely, if a gaseous hydrocarbon containing arsenic compounds is contacted with manganese oxide, copper oxide or mixtures thereof, the arsenic compound is reacted with the catalyst and adsorbed thereon. It is estimated that manganese arsenide MnAs is formed from manganese and copper arsenide $Cu_5As_2$ is formed from copper and the resultant manganese arsenide and copper arsenide are adsorbed on the catalyst metal oxides and removed from the hydrocarbon. If a portion of the arsenic compounds is oxidized by the catalyst and adsorbed on the catalyst, the arsenic compounds are easily separated from the hydrocarbon, e.g., by adsorption on the catalyst or optionally an additional distillation treatment. As a result, 95 weight % or more of the arsenic can be removed.

Reaction temperature according to the present method is 0°–80° C., preferably ambient to 60° C.

Reaction pressure according to the present method is 0–30 kg/cm² gauge, preferably 10–20 kg/cm² gauge.

Possible adsorption reactions are as follows.

$$2AsH_3 + Mn_2O_3 \rightarrow 2MnAs + 3H_2O$$

$$AsH_3 + MnO_2 \rightarrow MnAs + H_2O + \tfrac{1}{2}O_2$$

$$2AsH_3 + 2MnO \rightarrow 2MnAs + 2H_2O + H_2$$

$$2AsH_3 + 5CuO \rightarrow Cu_5As_2 + 3H_2O + O_2$$

$$3CH_3AsH_2 + 2MnO_2 \rightarrow 2MnAs + 2CH_4 + H_2 + 3/2 O_2$$

Figure 2:
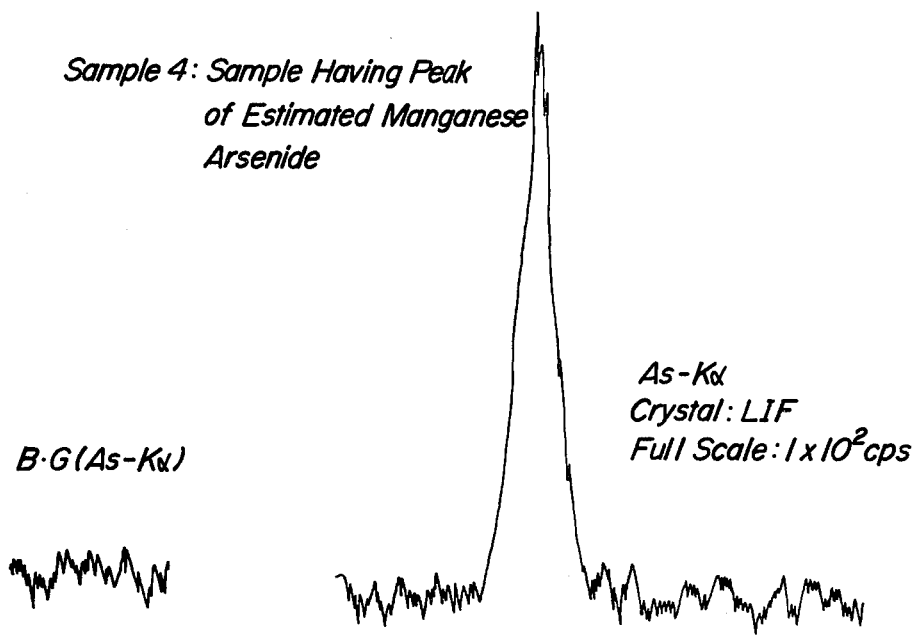
FIG. 2 is a graph showing an Electron probe analyzer of a catalyst recovered from a treatment according to the present invention, showing a peak of estimated manganese arsenide.
Figure 3:
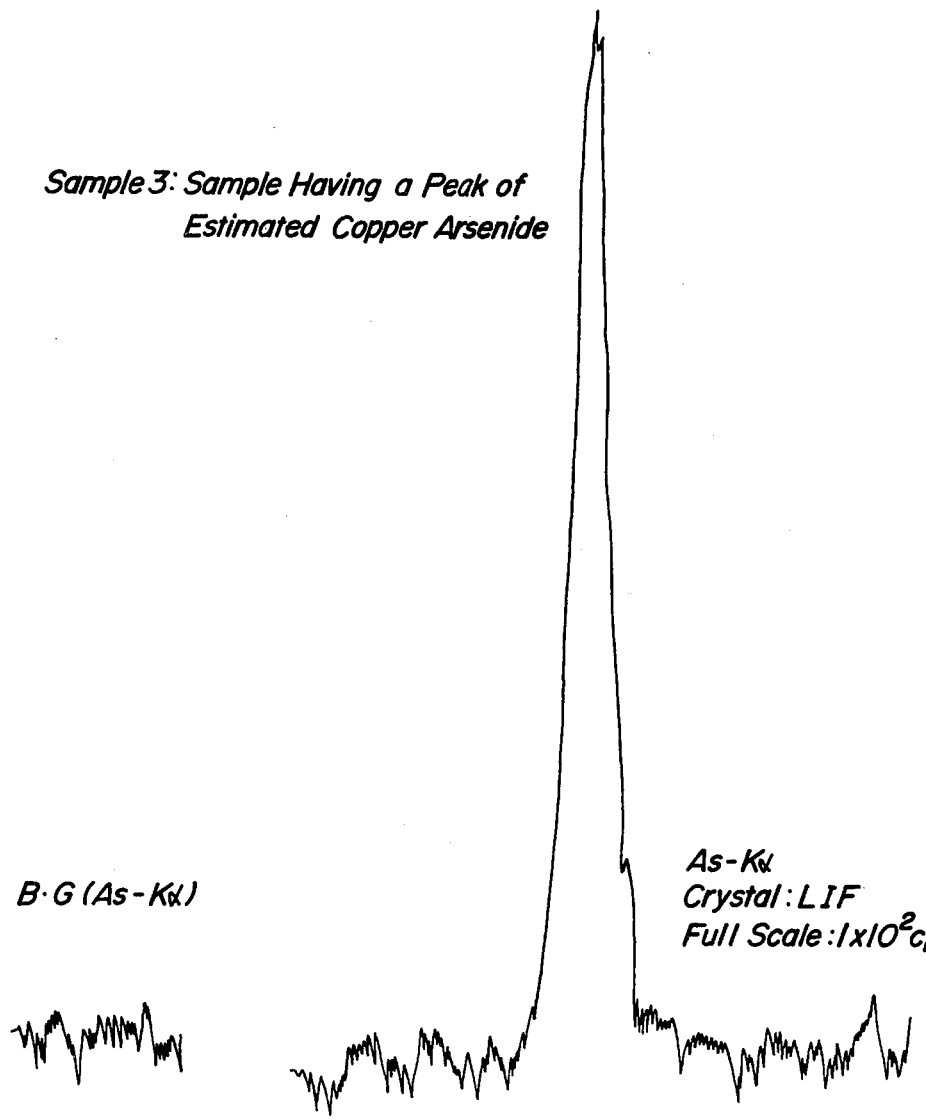
FIG. 3 is a graph showing an Electron probe analyzer of another catalyst recovered from a treatment according to the present invention, showing a peak of estimated copper arsenide.

Analytical results of arsenic contents of catalysts which were used for removing arsenic in a hydrocarbon and subjected to desorption treatment to desorb simple deposits at 150° C. under reduced pressure are shown in FIGS. 2 and 3.

The present invention has the following characteristic features: (1) no pretreatment other than vaporization of hydrocarbon is necessary (2) removal of arsenic is extremely high (95% or more) so that a large amount of gas can be treated and purified with a small amount of catalyst, and (3) even when unsaturated hydrocarbon is contained in the raw hydrocarbon, side reaction such as polymerization of the hydrocarbon on the catalyst scarcely occur; and arsenic compound can be removed smoothly.

The present invention is superior to with conventional methods in that it can remove minor amounts of arsenic compounds, particularly arsines such as $AsH_3$, $CH_3AsH_2$ and the like, in hydrocarbons and is economical in investment cost as well as operation cost.

Figure 1:
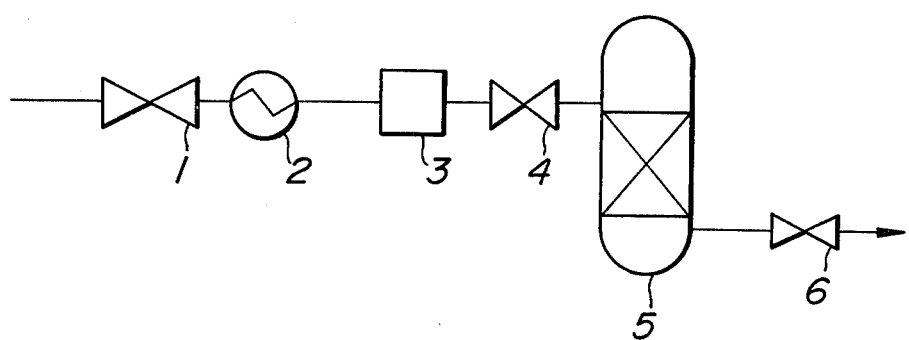
FIG. 1 is a schematic flow sheet showing the process of removing arsenic in hydrocarbons according to the present invention.

Hereinafter, the present invention will be explained in more detail with reference to working examples in conjunction with FIG. 1 which shows a flow sheet of the method of the present invention.

EXAMPLE 1

A gaseous $C_3LPG$ fraction produced from a fluidized bed type catalytic cracking apparatus of a petroleum refinery plant is charged in a catalytic reactor 5 having a diameter of 3 inches and a height of 1.5 meters and containing 4.0 kg of tablet-shaped manganese oxide of a diameter of 6 mm and a height of 3 mm through an inlet valve 1, a preheater 2 for preventing condensation of gas, a flow meter 3 and an inlet valve 4, and released through an exit valve 6. The results are shown in Table 1.

Raw material gas composition:

| | |
|---|---|
| Propylene | 92 mol % |
| Propane | 6 mol % |
| $C_2$ fraction such as $C_2H_4$, $C_2H_6$ | 1 mol % |
| $C_4$ fraction such as $C_4H_6$, $C_4H_{10}$ | 1 mol % |
| Operation pressure | 16.5 kg/cm$^2$ gauge |
| Operation temperature | 45° C. |
| Catalyst and quantity | Manganese oxide 4.0 kg |

TABLE 1

Operation Data in Removing Arsenic

| Condition | As in feed gas (mg/Nm$^3$) | Gas feed rate (Kg/H) | Superficial velocity in a column (m/min) | As in treated gas (mg/Nm$^3$) |
|---|---|---|---|---|
| 1 | 3.4 | 25.0 | 3.4 | <0.1 |
| 2 | 3.6 | 20.0 | 2.7 | <0.1 |
| 3 | 2.4 | 15.0 | 2.0 | <0.1 |
| 4 | 2.0 | 25.0 | 3.4 | <0.1 |
| 5 | 1.6 | 20.0 | 2.7 | <0.1 |

EXAMPLE 2

The sample operation as in Example 1 is repeated, except that the catalyst used is 3.9 kg of copper oxide instead of 4.0 kg of manganese oxide. The results are shown in the following Table 2. Removal percentages of arsenic compound are all excellent.

Raw material gas composition:

| | |
|---|---|
| Propylene | 92 mol % |
| Propane | 6 mol % |
| $C_2$ fraction such as $C_2H_4$, $C_2H_6$ | 1 mol % |
| $C_4$ fraction such as $C_4H_6$, $C_4H_{10}$ | 1 mol % |
| Operation pressure | 16.5 kg/cm$^2$ gauge |
| Operation temperature | 45° C. |
| Catalyst and quantity | Copper oxide 3.9 kg |

TABLE 2

Operation Data in Removing Arsenic

| Condition | As in feed gas (mg/Nm$^3$) | Gas feed rate (Kg/H) | Superficial velocity in a column (m/min) | As in treated gas (mg/Nm$^3$) |
|---|---|---|---|---|
| 1 | 3.4 | 15.0 | 2.0 | <0.2 |
| 2 | 3.2 | 12.0 | 1.6 | <0.2 |
| 3 | 2.4 | 8.0 | 1.1 | <0.2 |
| 4 | 2.0 | 15.0 | 2.0 | <0.1 |
| 5 | 1.6 | 12.0 | 1.6 | <0.1 |

EXAMPLE 3

The same operation as in Example 1 is repeated, except that the catalyst used is 3.1 kg of a mixture consisting of 85 weight % of manganese oxide and 15 weight % of copper oxide. The results are shown in the following Table 3. Removal percentages of arsenic compound are all excellent.

Raw material gas composition:

| | |
|---|---|
| Propylene | 92 mol % |
| Propane | 6 mol % |
| $C_2$ fraction such as $C_2H_4$, $C_2H_6$ | 1 mol % |
| $C_4$ fraction such as $C_4H_6$, $C_4H_{10}$ | 1 mol % |
| Operation pressure | 16.5 kg/cm$^2$ gauge |
| Operation temperature | 45° C. |
| Catalyst and quanity | A mixed catalyst 3.1 kg consisting of 85 weight % of manganese oxide and 15 weight % of copper oxide |

TABLE 3

Operation Data in Removing Arsenic

| Condition | As in feed gas (mg/Nm$^3$) | Gas feed rate (Kg/H) | Superficial velocity in a column (m/min) | As in treated as (mg/Nm$^3$) |
|---|---|---|---|---|
| 1 | 5.0 | 25.0 | 3.4 | <0.1 |
| 2 | 4.3 | 25.0 | 3.4 | <0.1 |
| 3 | 3.7 | 20.0 | 2.7 | <0.1 |
| 4 | 3.4 | 25.0 | 3.4 | <0.1 |
| 5 | 2.6 | 20.0 | 2.7 | <0.1 |

Although the present invention has been described in detail with reference to specific embodiments, it is understood that the present disclosure has been made only by way of example and that numerous changes and modifications can be made without departing from the aspect and scope of the present invention as hereinafter claimed.

What is claimed is:

1. A method of removing arsenic in gaseous hydrocarbons, particularly LPG, comprising reacting arsenic compounds in the gaseous hydrocarbon in a gas phase reaction at a temperature of 0°-80° C. under a reaction pressure of 0-30 kg/cm$^2$ with a metal oxide and retaining the resultant reaction product on said metal oxide, whereby the arsenic compound in the gaseous hydrocarbon is substantially removed therefrom.

2. A method as defined in claim 1, wherein the metal oxide comprises at least one metal oxide selected from the group consisting of manganese oxide, copper oxide and a mixture thereof.

3. A method as defined in claim 1, wherein the reaction temperature is ambient to 60° C.

4. A method as defined in claim 1, wherein the reaction pressure is 10-20 kg/cm$^2$.

5. A method as defined in claim 1, wherein a small portion of arsenic compound is oxidized by the metal oxide and retained on the metal oxide in the gas phase reaction.

* * * * *